United States Patent [19]

Hirsbrunner

[11] 4,399,128
[45] Aug. 16, 1983

[54] PHARMACEUTICAL CARRIER AND COMPOSITIONS

[75] Inventor: Pierre Hirsbrunner, Corseaux, Switzerland

[73] Assignee: Societe d'Assistance Technique pour Produits Nestle S.A., Lausanne, Switzerland

[21] Appl. No.: 393,507

[22] Filed: Jun. 29, 1982

[30] Foreign Application Priority Data

Aug. 28, 1981 [EP] European Pat. Off. ........ 81106715.6

[51] Int. Cl.³ ............................................. A61K 31/60
[52] U.S. Cl. ..................................................... 424/230
[58] Field of Search ........................................ 424/230

[56] References Cited

U.S. PATENT DOCUMENTS 3,608,064 9/1971 Lamb .................................. 424/359
4,003,989 1/1977 Bar-On .................................. 424/43

Primary Examiner—Stanley J. Friedman
Attorney, Agent, or Firm—Vogt & O'Donnell

[57] ABSTRACT

A pharmaceutical carrier or excipient comprises milk solids and tripotassium phosphate. It is especially suitable for preparing compositions containing moisture-sensitive active ingredients, which may also be acidic in character.

The carrier is especially suitable for compounding with ASA (acetylsalicylic acid) to give compositions which disperse readily on contact with water. The resulting solutions are buffered and contain neutralized ASA dissolved in a liquid milk phase.

15 Claims, No Drawings

PHARMACEUTICAL CARRIER AND COMPOSITIONS

This invention is concerned with a solid pharmaceutical carrier especially suitable for use with active ingredients that are sensitive to moisture. The invention is also concerned with compositions comprising the carrier and at least one active ingredient.

In the preparation of dry pharmaceutical compositions—such as powders or tablets, the active ingredient is homogeneously dispersed in a dry carrier, which is frequently lactose, together with appropriate adjuvants such as flavourings and for example binders in the case of tablets. When the active ingredient is sensitive to moisture, extensive precautions must be taken to ensure a reasonable storage life without loss of activity.

It has now been found that a combination of milk solids and tripotassium phosphate (potassium orthophosphate) constitutes an excellent carrier or excipient for use in powdered compositions containing a moisture-sensitive active ingredient. The invention thus provides a pharmaceutical carrier or excipient characterised in that it comprises milk solids and tripotassium phosphate, the amount of tripotassium phosphate present being at least sufficient to bind moisture associated with the milk solids.

Also provided are compositions comprising the carrier defined above and a moisture-sensitive active ingredient.

The milk solids are commonly in the form of milk powder, especially skimmed milk powder.

Since the stable form at ambient temperature is the octahydrate (cf. Gmelin, "Handbuch der anorganischen Chemie", 8th ed., Berlin 1938, Vol. 22, p. 992), it may be calculated that 1 gram of anhydrous tripotassium phosphate is capable of binding approximately 680 mg of water. Hence, for any given milk powder of known moisture content the amount of tripotassium phosphate required to bind the water can be easily calculated.

The carrier may be prepared by simple, thorough mixing of the ingredients in selected amounts. Instant skimmed milk powder is especially preferred, because of its rapid dispersibility in cold water. The tripotassium phosphate may be ground to a relatively fine particle size, such as about 100 microns.

In compounding pharmaceutical compositions comprising the carrier according to the invention, it is possible to form one or more pre-mixes. These include the active ingredient and milk solids as well as further additives such as flavourings, sweetenings and colourings together with the tripotassium phosphate. Again, it may be desirable to subdivide certain components to a very small particle size.

The pharmaceutical carrier or excipient according to the invention is especially suitable for formulating moisture-sensitive active ingredients that are acidic in character and essentially insoluble in water, for the tripotassium phosphate also acts as a neutralising and solubilising agent. In this case, the proportion of tripotassium phosphate in the composition should be at least sufficient to neutralise the acidic ingredient.

A particular example of such an acidic, moisture-sensitive active ingredient is acetylsalicylic acid (hereinafter ASA for short) and therefore another aspect of the invention relates to ASA compositions and their preparation.

ASA is a useful therapeutic agent having analgesic, antipyretic and anti-inflammatory properties. Large, sustained doses, however, can produce undesirable side-effects, including for example gastric symptoms, salicylism (deafness, vertigo, tinnitus) and allergy (see e.g. Vining et al., British Medical J., Feb. 23, 1957, p. 444). It is generally believed that ulceration occurs because ASA is essentially insoluble in the gastric juices and thus the solid particles cause considerable irritation and damage to the lining. Since gastric disturbances appear to be the most common, numerous ASA preparations have been devised to reduce gastric intolerance.

Thus, U.S. Pat. No. 3,608,064 describes compositions consisting of ASA and powdered milk, it being stated that the milk provides a natural alkaline barrier which minimises the possible (negative) effects. According to U.S. Pat. No. 4,003,989, the undesirable gastric effects of ASA are reduced by providing a solubilising agent together with milk powder. The compositions thus contain ASA, an alkaline carbonate and/or bicarbonate, and an amount of milk solids which is 10 to 100 times the weight of ASA.

Whilst the compositions of U.S. Pat. No. 4,003,989 do attenuate undesirable gastric symptoms, on mixing the powdered material with water, carbon dioxide is generated and ultimately an unappetising heterogeneous system results, consisting of a clear liquid covered with a layer of froth mixed with solid proteins precipitated by the carbonic acid formed. Moreover, because ASA is highly sensitive to water, to obtain a reasonable shelf-life the milk powder, normally containing 2–4% moisture, has to be dried to a moisture content below 0.5% by weight, which is highly impractical and uneconomical on a large scale.

It has now been found that a stable, dry ASA composition which, on contact with water or an edible aqueous liquid, disperses rapidly to provide a buffered solution of neutralised ASA in a continuous liquid phase containing dissolved milk solids may be prepared using tripotassium phosphate as a neutralising agent. The composition according to the invention is thus characterised in that it comprises ASA, milk solids and tripotassium phosphate in an amount sufficient to neutralise the ASA present. Tripotassium phosphate has a dual action—firstly, to neutralise the ASA, and secondly as a scavenger for moisture brought in with the milk solids, so that during storage the ASA is protected against decomposition by hydrolysis and consequent loss of activity. Moreover, the taste of potassium salts is perfectly acceptable. The milk solids are preferably non-fat milk solids, conveniently provided in the form of commercially available skimmed milk powder having a moisture content within the 2–4% range; the tripotassium phosphate may be anhydrous, but is usually the commonly-occurring monohydrate. Higher hydrates are much less desirable because of their reduced dehydrating capacities.

To provide for the desired solubilisation of ASA, the amount of tripotassium phosphate in the composition should be at least sufficient to neutralise the ASA and give a solution in the pH range 6.2–7.2, preferably 7.0–7.2. Thus, the compositions normally contain at least 0.5 mole tripotassium phosphate/mole ASA and preferably 0.85 to 0.9 moles/mole so that the pH of the reconstituted solution is 7.0–7.2. When the monohydrate is used an appropriate upward adjustment should be made; the moisture content of the milk solids should also be taken into account to ensure that sufficient water adsorption capacity is available in the composition. Milk solids, on a fat-free basis, are usually present in an amount corresponding to 3 to 20 times the weight of the other ingredients. Flavourings, colourings and/or sweeteners may also be added as required.

Preferably, the compositions are presented in dosage units, each being sufficient for mixing with 50 to 100 ml of water or other aqueous liquid. Powders are the most preferred form, as they are easily dispersed. The amount of ASA per dosage unit will be chosen having regard to the intended user—i.e. smaller amounts will be present in formulations intended for children—e.g. 50 to 100 mg/unit, whereas an adult dose will normally contain 300 to 600 mg of ASA per unit. The flavourings, colourings and sweeteners will also be chosen to suit the users' tastes and preferences.

In preparing the compositions, best results in terms of homogeneity and storage life are obtained when certain precautions are taken in combining the ingredients. Thus, the tripotassium phosphate and any solid sweeteners and flavourings should be finely ground—average particle size preferably not exceeding 100 microns. Usually, the tripotassium phosphate should first be mixed with a part of the milk solids (instant skimmed milk powder for preference) and likewise the ASA. Thereafter the two pre-mixes are combined and thoroughly blended with the remainder of the milk solids. Any flavourings, sweeteners and colourings may be added to the tripotassium phosphate pre-mix. Thereafter, the blend may be filled into sachets or other suitable containers in amounts corresponding to the desired dose of ASA. The containers should be moisture-impermeable and be sealed accordingly.

On mixing with water or other aqueous liquids the compositions according to the invention form a buffered milky solution of neutralised ASA which is pleasant to consume. The solubilised active ingredient is rapidly absorbed in the intestine so that the unpleasant gastric symptoms described above are largely avoided.

The following Examples, in which all parts and percentages are expressed on a weight basis, are given for the purposes of illustration only.

EXAMPLE 1

2 parts of vanillin and 8 parts of sodium saccharin are ground finely (average particle size not exceeding 100 microns) and mixed with 38 parts of tripotassium phosphate monohydrate (TPM for short), which has likewise bean finely ground. 30 parts of instant skimmed milk powder are then added, giving the first pre-mix. The second pre-mix is prepared by mixing 33 parts of ASA with 40 parts of instant skimmed milk powder. The pre-mixes are then thoroughly blended together with 849 parts of instant skimmed milk powder and the batch filled into moisture-impermeable sachets each containing 3 grams.

The composition contains

| ASA | 3.3% |
|---|---|
| TPM | 3.8 |
| Milk solids | 91.9 |
| Vanillin | 0.2 |
| Na saccharin | 0.8 | and is suitable for children.

EXAMPLE 2

A formulation suitable for adults is prepared as described in Example 1 except that the ASA is increased to 100 parts with a corresponding adjustment in the amount of TPM to 112 parts. The flavouring and sweetener levels are also higher with an overall decrease in milk solids. The final powdered composition thus contains

| ASA | 10.0% |
|---|---|
| TPM | 11.2 |
| Milk solids | 78.0 |
| Vanillin | 0.16 |
| Na saccharin | 0.64 | and it is also filled and sealed in moisture-impermeable sachets at 5 gm each.

In both Examples a commercially available instant skimmed milk powder having a moisture content of 2.1% was used.

The compositions of Examples 1 and 2, as packed in sachets were stored for 3 months at 37° C. At the end of this period the flavour and aspect of the product were unaltered and the degree of hydrolysis of the ASA was below 3%.

I claim:

1. A stable, dry ASA (acetylsalicylic acid) composition which on contact with water disperses rapidly to provide a buffered solution of neutralised ASA in a continuous liquid phase containing dissolved milk solids, characterised in that it contains an effective amount of ASA, milk solids in an amount where the weight ratio of the milk solids (expressed on a non-fat basis) to all other ingredients is 3 to 20:1, and tripotassium phosphate in an amount sufficient to neutralise the ASA.

2. A composition according to claim 1 containing at least 0.5 mole tripotassium phosphate per mole of ASA.

3. A composition according to claim 1 or claim 2 in which the weight ratio of tripotassium phosphate to ASA is such that on reconstitution with water a solution having a pH of 6.2 to 7.2 is obtained.

4. A composition according to claim 3 in which the ratio of tripotassium phosphate to ASA is 0.85 to 0.9 and a solution having a pH of 7.0–7.2 is obtained.

5. A composition according to claim 1 in which the tripotassium phosphate has a particle size not exceeding 100 microns.

6. A composition according to claim 1 in which the milk solids are skimmed milk powder.

7. A composition according to claim 1 also containing at least one of a flavouring, a sweetening agent and a colouring.

8. A composition according to claim 1 in dosage unit form.

9. A pharmaceutical carrier or excipient in powder form characterised in that it comprises milk solids and tripotassium phosphate in an amount sufficient to bind moisture associated with the milk solids.

10. A pharmaceutical composition comprising a carrier according to claim 9 and an effective amount of a moisture-sensitive active ingredient.

11. A process for preparing a composition according to claim 1 comprising 3 to 20 parts by weight of milk solids per part by weight of all other ingredients taken together and which contains at least 0.5 moles of tripotassium phosphate per mole of ASA, the process being characterised in that a first pre-mix containing the tripotassium phosphate and a portion of the total milk solids, and a second pre-mix containing the ASA and a further portion of the total milk solids are formed and thereafter the first and second pre-mixes are blended with the balance of the milk solids, the moisture content of the milk solids used being 2 to 4% by weight.

12. A process according to claim 11 in which the first pre-mix also contains at least one of a flavouring, a sweetening agent and a colouring.

13. A process according to claim 11 or claim 12 in which the milk solids are skimmed milk powder.

14. A process according to claim 11 or claim 12 in which the tripotassium phosphate has a particle size not exceeding 100 microns.

15. A process for preparing a pharmaceutical composition according to claim 10 which comprises combining skimmed milk powder having a moisture content of 2–4% by weight, tripotassium phosphate and a moisture-sensitive active ingredient.

* * * * *